United States Patent [19]

DiGiacomo

[11] 4,000,742
[45] Jan. 4, 1977

[54] WALL MOUNTED HYGIENIC DEVICE

[76] Inventor: Edward F. DiGiacomo, 6930 NW. 186th St., Apt. 302, Hialeah, Fla. 33015

[22] Filed: Oct. 20, 1975

[21] Appl. No.: 623,768

[52] U.S. Cl. .............................. 128/229; 128/251; 4/7

[51] Int. Cl.$^2$ ........................................ A61M 3/00

[58] Field of Search ............ 128/229, 66, 247, 248, 128/173.1, 251; 239/310, 316, 427; 137/798, 799; 251/149.6; 4/6, 7, 191, 192; D23/4, 8, 49, 51, 43, 44

[56] References Cited

UNITED STATES PATENTS

| 574,236 | 12/1896 | Blackburn | 128/247 X |
|---|---|---|---|
| 1,680,762 | 8/1928 | Butler et al. | 128/229 X |
| 1,887,359 | 11/1932 | Marubio | 128/229 |
| 1,950,680 | 3/1934 | Johns | 128/229 |
| 2,103,957 | 12/1937 | Scott | 128/229 X |
| 2,180,790 | 11/1939 | Brummett | 4/192 |
| 2,241,823 | 5/1941 | McFarland et al. | 4/7 X |
| 2,257,072 | 9/1941 | Coombs | 128/227 |
| 2,829,645 | 4/1958 | Matteson | 128/229 |
| 2,957,476 | 10/1960 | Freeman | 128/229 |
| 3,065,746 | 11/1962 | Gregory | 128/66 |
| 3,577,567 | 5/1971 | Wintercorn | 4/7 |
| 3,704,002 | 11/1972 | Skarzynski | 251/149.6 |
| 3,715,099 | 2/1973 | Shendure | 251/149.6 X |
| 3,769,977 | 11/1973 | Victory | 128/251 |

*Primary Examiner*—J. Reed Fisher
*Attorney, Agent, or Firm*—Salvatore G. Militana

[57] ABSTRACT

A hygienic device having a plate that is adapted to be mounted on a wall and the like with fittings thereon connected to a source of hot and cold water with a valve for adjusting the amount of hot water to be mixed with the cold water; the mixture then flowing through a fitting mounted on the plate having a slide valve that is normally closed but is opened upon inserting a quick coupler device therein. The quick coupler is provided with a receptacle for containing a medicine and a venturi into which the medicine is permitted to mix with the water that is then discharged through a douche nozzle.

1 Claim, 3 Drawing Figures

WALL MOUNTED HYGIENIC DEVICE

BACKGROUND OF THE INVENTION

1. Field Of The Invention

This invention relates to hygienic devices and is more particularly directed to a wall mounted hygienic device for home use.

2. Description Of The Prior Art

At the present time only institutions such as hospitals have hygienic devices of the irrigation type mounted permanently on a wall or cabinet. These devices are complicated, expensive and unsightly to say the least. For these reasons, very few if any homes have a permanently mounted irrigation device in their bathrooms. Most persons use at home, the bag-type douche or irrigation device that utilize gravity to compel the water to flow therethrough. In these devices the discharge of the mixture of water and medication is not at a sufficiently high pressure to effect a proper cleansing action.

The present invention contemplates having a wall mounted hygienic device that provides a discharge of the mixture of water and medication at top pressures.

BRIEF SUMMARY OF THE INVENTION

Therefore, a principal object of the present invention is to provide a hygienic device that is mounted on a wall in a sightly manner, is simple in design and construction and most effective in its cleansing action as in a douche and the like.

Another object of the present invention is to provide a hygienic device having a plate that is adapted to be mounted on the wall of a bathroom and fittings secured to the plate connected to sources of cold and hot water on the rear face of the plate and switches mounted on the face of the plate for controlling the mixture of hot and cold water.

A further object of the present invention is to provide a hygienic device with a plate adapted to be mounted on a wall and having a slide valve fitting secured to the plate with its valve in a normally closed position and a quick coupler which upon being connected to the fitting effects the opening of the valve to permit water to flow therethrough.

A still further object of the present invention is to provide a hygienic device with a quick coupler having a venturi passageway therethrough and a medicine bowl mounted thereon connected to the venturi and to permit medication to be aspirated by and into the water flowing through the venturi.

With these and other objects in view, the invention will be best understood from a consideration of the following detailed description taken in connection with the accompanying drawing forming a part of this specification, with the understanding, however, that the invention is not confined to any strict conformity with the showing of the drawing but may be changed or modified so long as such changes or modifications mark no material departure from the salient features of the invention as expressed in the appended claims.

DETAILED DESCRIPTION OF THE PREFERRED EMBODIMENT

Figure 1:
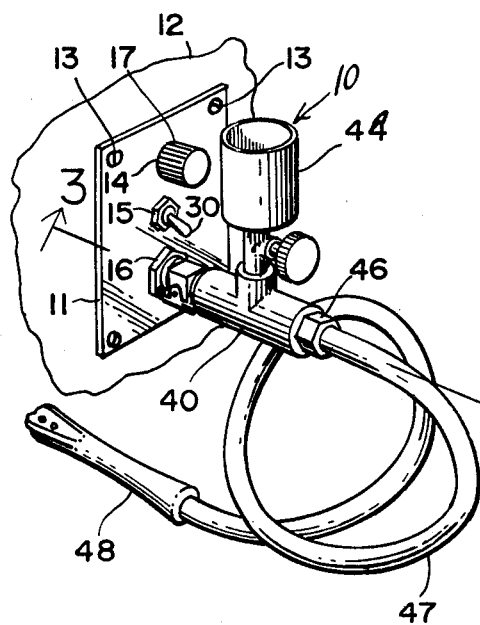
FIG. 1 is a perspective view of a hygienic device constructed in accordance with my invention and shown mounted on a plate which is attached to a wall shown only in part.
Figure 2:
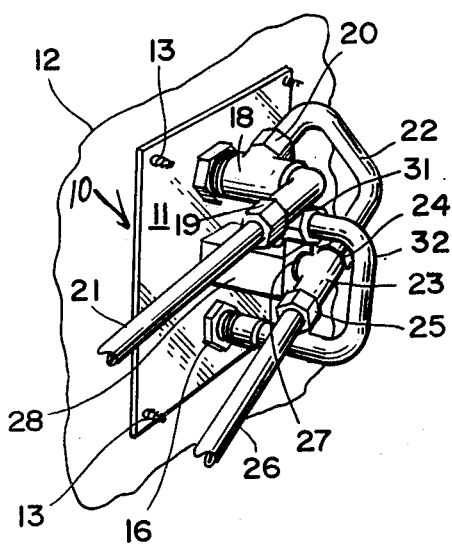
FIG. 2 is a similar view showing the obverse side of that shown by FIG. 1.
Figure 3:
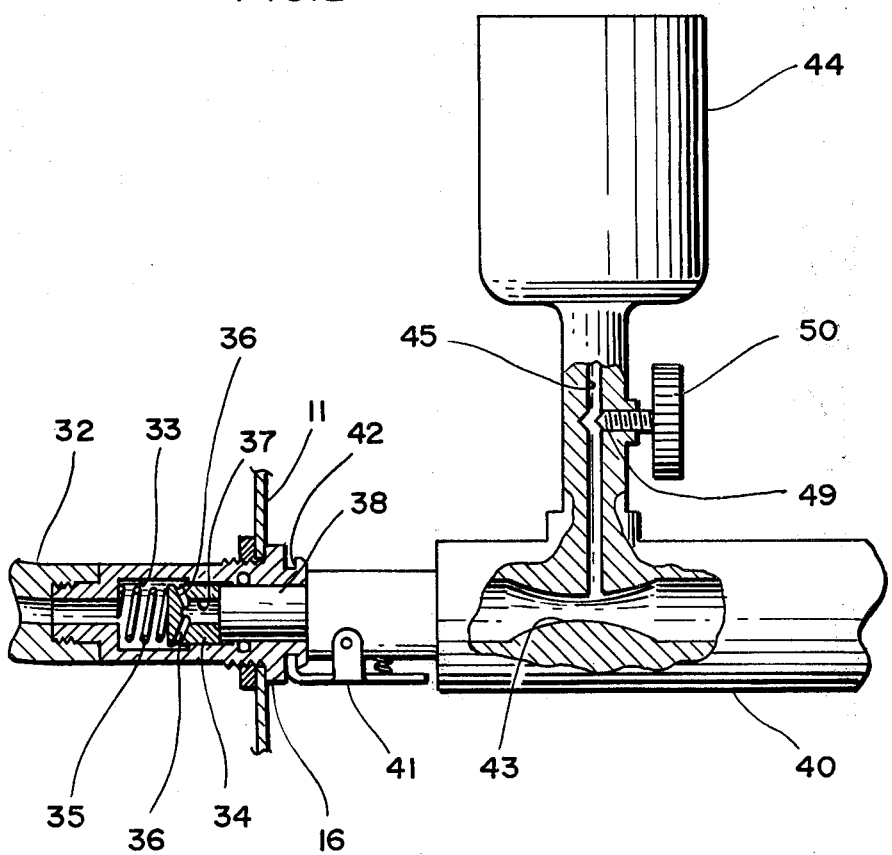
FIG. 3 is a cross sectional view taken along the line 3—3 of FIG. 1.

Referring to the drawing wherein like numerals are used to designate similar parts throughout the several views, the numeral 10 refers to my hygienic device shown mounted on a plate 11 which in turn is secured to a wall 12 such as a bathroom wall by screws 13. Mounted on the plate 11 is a plurality of fittings 14, 15 and 16. At the front face of the plate 11, there is mounted on the fitting 14 a valve control knob 17 that extends into a valve housing 18 in which a conventional water control valve (not shown) is mounted. The valve housing 18 that is connected to the fitting 14 on the rear face of the plate 11 is provided with an inlet 19 and an outlet 20. The inlet 19 is connected by tubing 21 that extends to a source of hot water such as a water heater (not shown). The outlet 20 is connected by tubing 22 whose other end is connected to the hot water inlet 24 of a T-fitting 23 connected to tubing 26 that extends to a source (not shown) of cold water. The outlet 27 of the T-fitting 23 is connected to a valve housing 28 which contains a conventional valve (not shown) that permits the mixing of the cold and hot water passing through the inlets 24 and 25. The housing 28 which is mounted on the rear face of the plate 11 is connected to the fitting 15. On the front face of the plate 11 and mounted on the fitting 15 is a toggle switch 30 which may be actuated to open or close the mixing valve contained in the housing 28. The housing 28 is provided with an outlet 31 to which tubing 32 is connected at one end with its other end extending to the valve fitting 16. The fitting 16 is provided with a chamber 33 in which a valve member 34 is slidably positioned with a spring 35 yieldingly forcing the valve member 34 in a closed position. In order to arrive at its open position, the valve member 34 must slide against the spring pressure 35 to expose the passageways 36 to the chamber 33 and permit the water to flow from the tubing 32 through the chamber 33, the passageways 36 and the outlet 37. The valve member 37 is automatically brought to its open position upon the insertion of the nipple portion 38 of a quick coupler 40 into the valve fitting 16. The nipple portion 38 engages the slide valve 34 to slide the valve 34 against the spring 35 to its open position. The quick coupler is provided with a spring actuated catch 41 which engages a slot 42 formed about the periphery of the fitting 16.

The quick coupler 40 is provided with a venturi passageway 43 which communicates with the outlet 37 of the valve 34. Mounted on the quick coupler 40 is an open receptacle 44 for containing a medication which flows through a passageway 45 to be aspirated into the venturi 43. The mixture is then discharged through outlet 46 to which a flexible tubing 47 is connected. At the free end of the flexible tubing 47 there is connected a douche nozzle 48, though any type of discharge nozzle may be used to accomplish a desired function, such as a simple discharge nozzle for cleansing purposes as in a bidet. The rate of flow of medication from the receptacle 44 is controlled by a needle valve 49 which is provided with a valve adjusting knob 50.

In preparing for the use of my hygienic device 10 for use as in a douche, the medicant in fluid form is placed in the medicine bowl 44 while the needle valve 49 is in its closed position. The toggle switch 30 is then flipped to its open position permitting the cold water under normal tap pressures to flow through the tubing 26, the valve housing 28, the tubing 32, the venturi passageway 43 and the flexible hose 47 to be discharged through the douche nozzle 48. The valve control knob 17 is then adjusted to control the amount of hot water to flow through the tubing 21, housing 18, tubing 22 and mix with the cold water at the T-fitting 23 and to be discharged at the douche nozzle 48 with the cold water at the desired temperature. At this time, the knob 50 is adjusted to open the needle valve 49 to the degree permitting the proper amount of medicine to flow from the medicine bowl 44, the ratio of medicant to water being approximately 1 to 100 parts. When the user of the device 10 is finished, the spring latch 41 is actuated to remove the quick coupler 40 from the fitting 16 and stored. The valve 34 will slide to its closed position preventing any loss or leakage of water therefrom.

What I claim as new and desire to secure by Letters Patent is:

1. A hygienic device adapted to be mounted on a wall and the like comprising a plate member, a plurality of fittings mounted on said plate, first tubing for cold water connected to one of said fittings, second tubing for hot water connected to the second of said fittings, first valve means mounted in the said second of said fittings for controlling the rate of flow of hot water therethrough, third tubing connecting said second of said fittings with said one of said fittings permitting the mixing of said hot and cold water, said one of said fittings having a first outlet, second valve means mounted in said one of said fittings controlling the discharge of mixed hot and cold water through said first outlet, fourth tubing connecting said first outlet and the third of said fittings, said third of said fittings having a second outlet, a slide valve mounted in said third of said fittings, spring means yieldingly maintaining said slide valve in a closed position and quick coupler means received by said third of said fittings at said second outlet engaging and sliding said slide valve to an open position for discharging said mixture of hot and cold water through said quick coupler means, said quick coupler means having an inlet, a discharge outlet, and a venturi connecting said inlet and said discharge outlet, an open receptacle mounted on said quick coupler means, a passageway connecting said receptacle and said venturi and needle valve means controlling the flow of fluid from said receptacle into said venturi, flexible hose means connected to said discharge outlet at one end and a nozzle connected to the free end of said flexible hose.

* * * * *